United States Patent
Weitzner et al.

(10) Patent No.: US 7,618,413 B2
(45) Date of Patent: Nov. 17, 2009

(54) MEDICAL DEVICE CONTROL SYSTEM

(75) Inventors: Barry Weitzner, Acton, MA (US); John Golden, Norton, MA (US); Frank T. McDonald, Bedford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 531 days.

(21) Appl. No.: 11/165,593

(22) Filed: Jun. 22, 2005

(65) Prior Publication Data

US 2007/0010800 A1    Jan. 11, 2007

(51) Int. Cl.
*A61B 17/00* (2006.01)

(52) U.S. Cl. ............ 606/1; 600/101; 600/146; 604/95.04

(58) Field of Classification Search ........... 600/146, 600/148, 149, 101, 104; 604/95.04; 606/1
See application file for complete search history.

(56) References Cited

U.S. PATENT DOCUMENTS

| | | | | | |
|---|---|---|---|---|---|
| 3,949,757 A | * | 4/1976 | Sabel | ............ | 607/123 |
| 4,826,087 A | * | 5/1989 | Chinery | ............ | 239/551 |
| 5,254,088 A | * | 10/1993 | Lundquist et al. | ...... | 604/95.04 |
| 5,284,130 A | * | 2/1994 | Ratliff | ............ | 600/229 |
| 5,325,845 A | * | 7/1994 | Adair | ............ | 600/114 |
| 5,462,527 A | * | 10/1995 | Stevens-Wright et al. | ... | 604/528 |
| 5,813,813 A | * | 9/1998 | Daum et al. | ............ | 414/7 |
| 6,007,482 A | * | 12/1999 | Madni et al. | ............ | 600/115 |
| 6,066,090 A | * | 5/2000 | Yoon | ............ | 600/113 |
| 6,156,027 A | * | 12/2000 | West | ............ | 604/528 |
| 2003/0050649 A1 | | 3/2003 | Brock et al. | | |
| 2004/0181140 A1 | * | 9/2004 | Falwell et al. | ............ | 600/374 |
| 2004/0193016 A1 | * | 9/2004 | Root et al. | ............ | 600/146 |
| 2004/0236316 A1 | | 11/2004 | Danitz et al. | | |
| 2005/0054899 A1 | * | 3/2005 | Miyake | ............ | 600/152 |
| 2005/0075538 A1 | * | 4/2005 | Banik et al. | ............ | 600/141 |
| 2005/0096694 A1 | | 5/2005 | Lee | | |

FOREIGN PATENT DOCUMENTS

| WO | WO 94/21179 A2 | 9/1994 |
|---|---|---|
| WO | WO 97/12557 A1 | 4/1997 |

* cited by examiner

*Primary Examiner*—Linda C Dvorak
*Assistant Examiner*—Samuel Candler
(74) *Attorney, Agent, or Firm*—Finnegan Henderson Farabow Garrett & Dunner LLP

(57) ABSTRACT

A control system for allowing a physician to control the orientation of a medical device or a medical instrument in a variety of directions with one hand. An actuator selectively tensions one or more control cables having ends secured at or adjacent a distal tip of the medical device in order to bend the distal tip in a desired direction. In one embodiment, a physician can adjust the movement of the distal tip in a desired direction without affecting the orientation of the medical device in other directions.

14 Claims, 6 Drawing Sheets

US 7,618,413 B2

MEDICAL DEVICE CONTROL SYSTEM

FIELD OF THE INVENTION

The present invention relates to medical devices in general, and in particular, to devices for manipulating steerable medical devices or other minimally invasive tools within a patient's body.

BACKGROUND OF THE INVENTION

Steerable medical devices and other minimally invasive surgical tools are being increasingly used to perform medical procedures inside a patient's body. Steerable devices generally include an elongated sheath and one or more control cables having distal ends secured at or adjacent the distal tip of the sheath. A control knob or lever selectively tightens the control cables in order to bend the device in a desired direction. The problem with most medical device controllers is that they require two hands in order to move the distal tip of a device in more than one plane. Alternatively, in those designs where a user can move the distal tip in four directions with one hand, two hands are still required in order to advance, retract, or rotate the device. Although some robotic systems have been proposed to allow a physician to direct a distal tip of a device in any direction using motors, these systems are generally expensive and complicated.

Given these problems, there is a need for a control system that allows a physician to manipulate a minimally invasive medical device in any desired direction with a single hand. In addition, the system should be low cost and easy to manufacture.

SUMMARY OF THE INVENTION

The present invention is a control system for selectively orienting the distal tip of a steerable medical device. In one embodiment, the control has a body with an actuator that can be independently moved in at least two directions so movement of the actuator in each direction moves the distal tip of the medical device in a plane. In one embodiment, the control may be mounted on a rail that is fixed with respect to the location of a patient such that advancement retraction of the control on the rail causes a corresponding advancement, retraction, or rotation of the medical device. In one particular embodiment, the actuator allows movement of the distal tip in one plane to be decoupled from movement in another plane.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
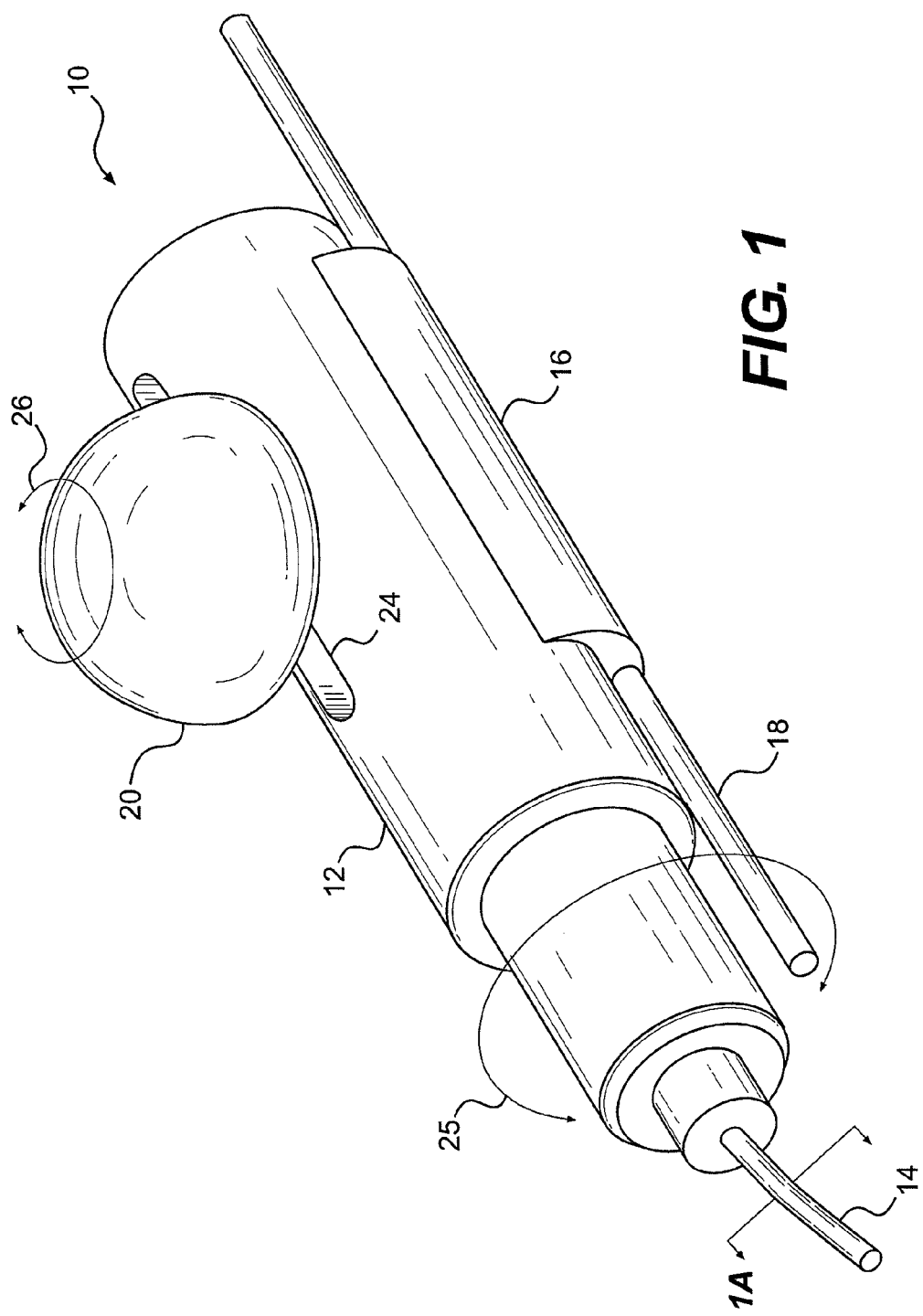
FIG. 1 is an elevated isometric view of a medical device control system in accordance with one embodiment of the present invention.
Figure 1A:
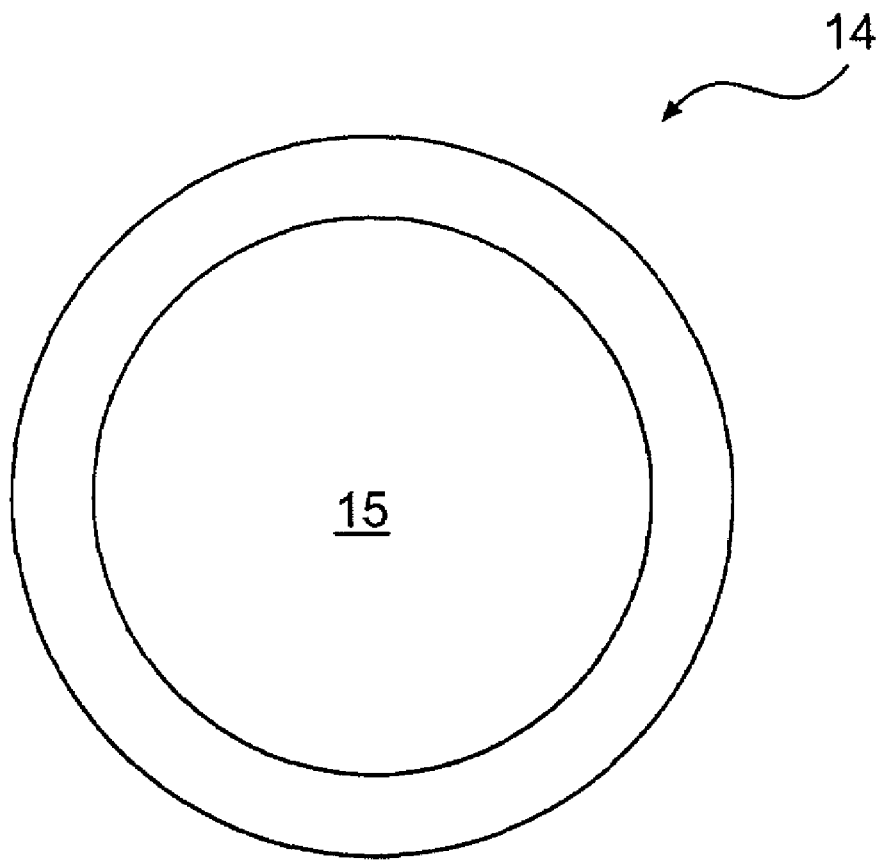
FIG. 1A is a cross-sectional view of the medical device shown in FIG. 1, in accordance with one embodiment of the present invention.

As indicated above, the present invention is a control system for selectively orienting a steerable medical device in a number of directions with one hand. In one embodiment of the invention, the control 10 includes a ergonomic, generally cylindrical body 12 having an actuator (described below) that operates to selectively tighten or release control cables that cause the distal tip of a medical device 14 such as a catheter, visualization device or instrument to bend in a desired direction. The body 12 includes one or more clamps 16 that allow it to be moved along a length of a rail 18 in order to advance or retract the medical device 14 as well as to provide rotation of the medical device around its longitudinal axis. The clamps 16 may provide a friction force that is overcome by a user in order to move the body 12 along the rail. Alternatively, the clamps 16 may include release mechanisms such as a brake or lock that should be unlocked to adjust the position of the body with respect to the rail 18. In yet another embodiment, the clamps 16 and rail 18 include a gear to move the body 12. The rail 18 may be clamped to a patient table or otherwise remain fixed with respect to the location of the patient such that the position of the medical device 14 remains constant if the physician's hand is removed from the control 10.

The control 10 can be rotated about the longitudinal axis of the rail 18 in the direction of the arrow 25 in order to impart rotational motion or torque to the medical device 14. Although the center axis of the medical device 14 is offset from the central axis of the rail 18, the medical device 14 is usually routed through a guiding device such as an endoscope or other constraining mechanism such that movement of the control 10 about the axis of the rail 18 causes the distal tip of the medical device 14 to rotate around the longitudinal axis of the device.

Finally, the control 10 includes an actuator 20 that is used by a physician, or their assistant, in order to move the distal tip of the medical device 14 in one or more of the up/down or right/left directions. In one embodiment, the actuator 20 can be moved forward or backward within a slot 24 that extends longitudinally along the top of the body 12 in order to move the distal tip of the medical device 14 up or down. In addition, the actuator 20 can be rotated as indicated by the arrow 26 in order to move the distal tip in the right/left direction. As will be explained in further detail below, movement of the distal tip in the up/down direction is decoupled from movement of the distal tip in the right/left direction so that a physician can maintain the orientation of the distal tip in the up/down direction while changing the right/left orientation or vice versa. Using the control 10, the physician is able to adjust the orientation of the distal tip with one hand, thereby allowing the physician to perform more intricate operations within the patient.

Figure 2:
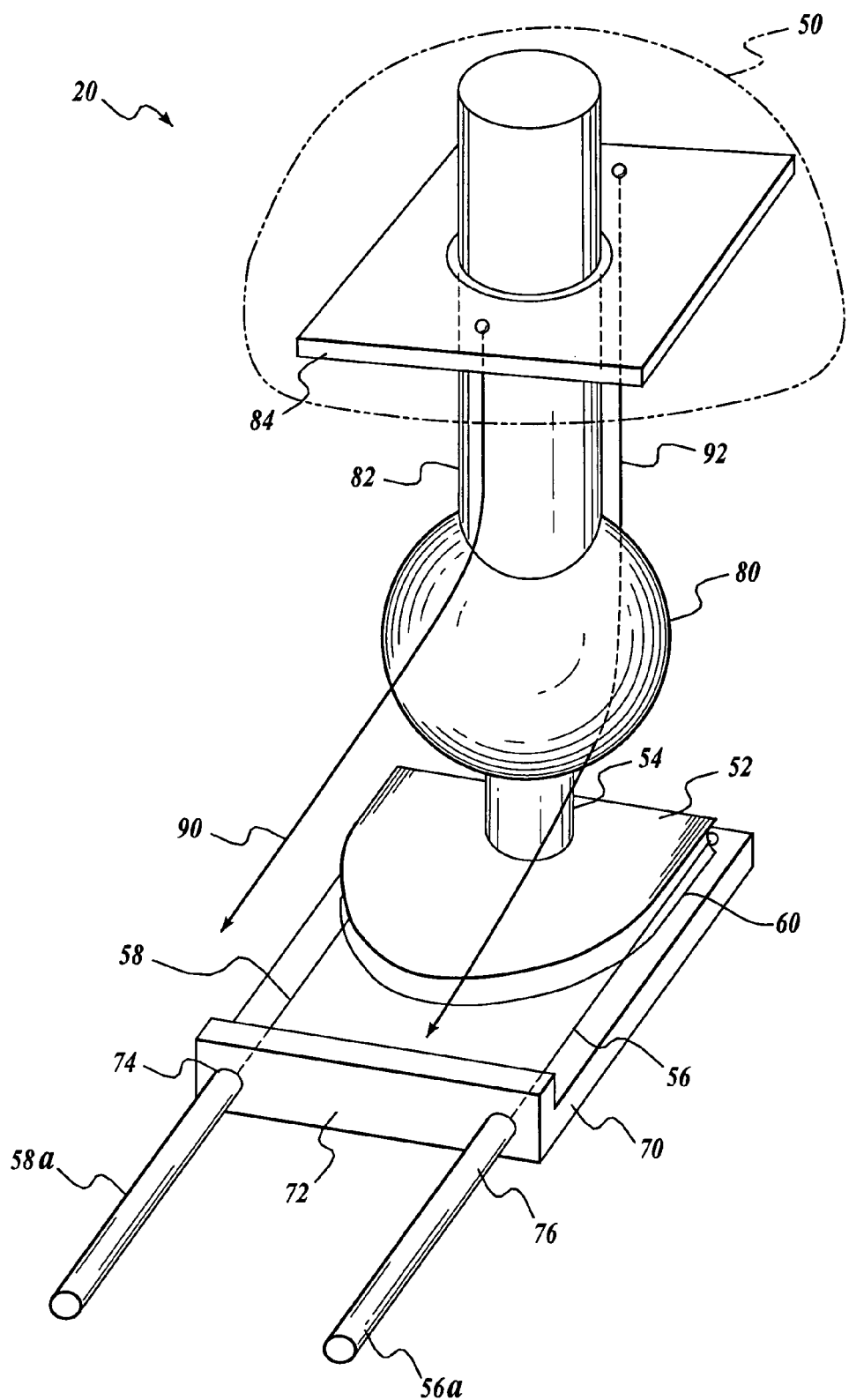
FIG. 2 illustrates one embodiment of an actuator for moving a medical device in accordance with the present invention.

As indicated above, the present invention allows an operator to adjust the orientation of a medical device with four degrees of freedom (up/down, left/right, forward/backward and rotationally) using one hand. FIG. 2 illustrates one embodiment of an actuator 20 for allowing a physician to change the up/down and right/left orientation of a distal tip of a medical device. The actuator 20 has a cap 50 that is connected to a cable guide plate 52 through a shaft 54. Rotation of the cap 50 about the longitudinal axis of the shaft 54 causes tension of one pair of control cables 56, 58. Tension of the control cable 56 causes a medical device tip to bend in the left direction, while tension on a control cable 58 causes a medical device tip to move in the rightward direction. The cable guide plate 52 is generally semi-circular in shape, with a rounded front end and a groove 60 therein to guide the corresponding control cables 56, 58. In the embodiment shown, the rear face of the cable guide plate 52 is generally flat. The ends of the control cables 56, 58 may be either fixedly secured to the cable guide plate 52 or slidably secured to the guide plate. If fixedly secured to the cable guide plate 52, then one control cable is tensioned while the other control cable is compressed as the cable guide plate is rotated by the cap 50. If the ends of the control cables are slidably secured to the cable guide plate, then one control cable is tensioned and the other is released from tension as the cable guide plate 52 is rotated. In some embodiments, the medical device 14 is permanently secured to the body 12 of the control. In other embodiments, the medical device is releasably secured to the body 12 by including cable connectors or the like that join the control cables in the medical device to the control cables in the body 12.

Also secured to the shaft 54 at a location adjacent the control cable guide plate 52 is a stop plate 70. The stop plate 70 has a raised lip 72 with a pair of holes 74, 76 therein through which the control cables 56, 58 are passed. Each of the control cables 56, 58 are preferably bowden cables, whereby the holes 74, 76 are sized such that the inner control cable of the bowden-type cables passes through the holes but the outer sheaths 56a, 56b of the bowden cables are too large to fit through the holes 74, 76. The stop plate 70 is shaped so that it does not rotate in the body of the control 10 when the actuator 20 is rotated around the axis of the shaft 54, but does move within the body of the control as the actuator is tilted back and forth. The stop plate 70 allows the physician to adjust the left/right position of the medical device 14 without adjusting the up/down position or vice-versa as will be explained below.

A ball joint 80 on the shaft 54 cooperates with a corresponding socket (not shown) in the interior of the body 12 of the control 10. A collar 82 is slidably mounted to the ball joint 80 and around the shaft 54. A top plate 84 is secured to the other end of the collar 82 and has a hole through which the shaft 54 is passed. The top plate secures the proximal ends of a pair of control cables 90, 92 that control the up/down movement of the medical device. The ball joint 80 allows the actuator 20 to be tilted back and forth with the interior of the body 12. Movement of the cap 50 towards the proximal end of the control 10 causes the control cable 90 to tighten, thereby causing the distal end of the medical device to move upwards. Similarly, pushing the cap 50 in the direction of the distal end of the control 10 causes the control cable 92 to tighten thereby causing the distal end of the medical device to move downwards.

Movement of the actuator 20 forwards and backwards about the axis of the ball joint 80 does not cause the distal tip of the medical device to move in the left/right direction. Similarly, rotation of the cap 50 about the longitudinal axis of the shaft 54 does not cause movement of the distal tip in the up/down direction. Therefore, the orientation of the medical device can be independently controlled in the up/down or right/left directions.

In some instances the control cables may be difficult to move with manual power alone. Therefore the actuator 20 may include a power assist mechanism to aid in tensioning the control cables. Such power assist may include hydraulic or pneumatic actuators, electric motors, magnets etc. that provide the additional force required to orient the distal tip of the medical device 14 in the desired direction.

Figure 3A:
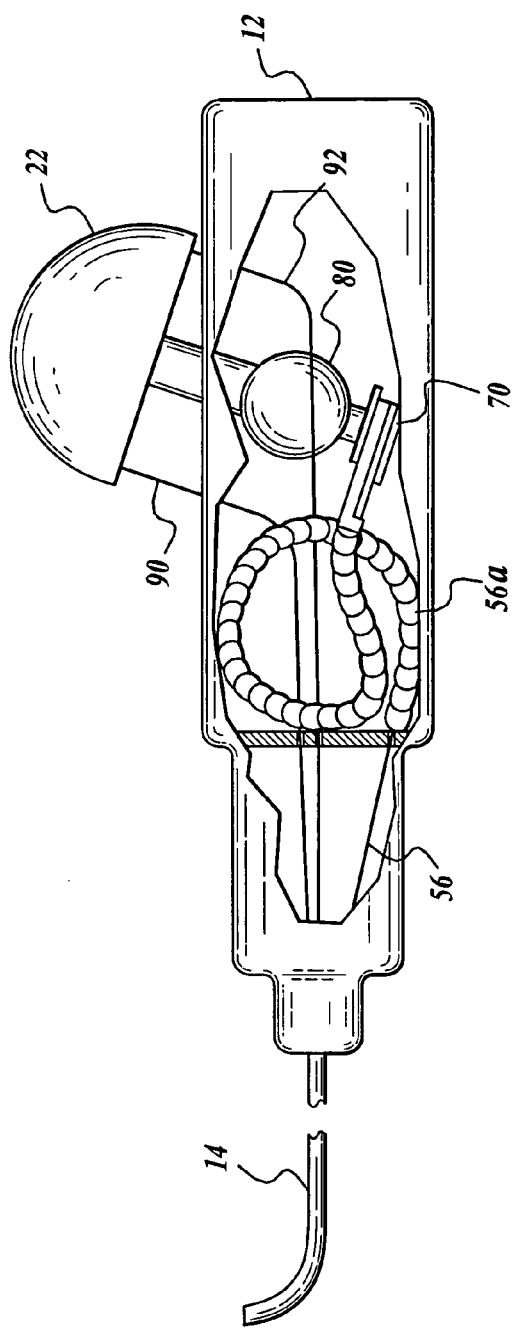
FIGS. 3A and 3B illustrate how an embodiment of the invention isolates movement of the distal tip of a controlled medical device.
Figure 3B:
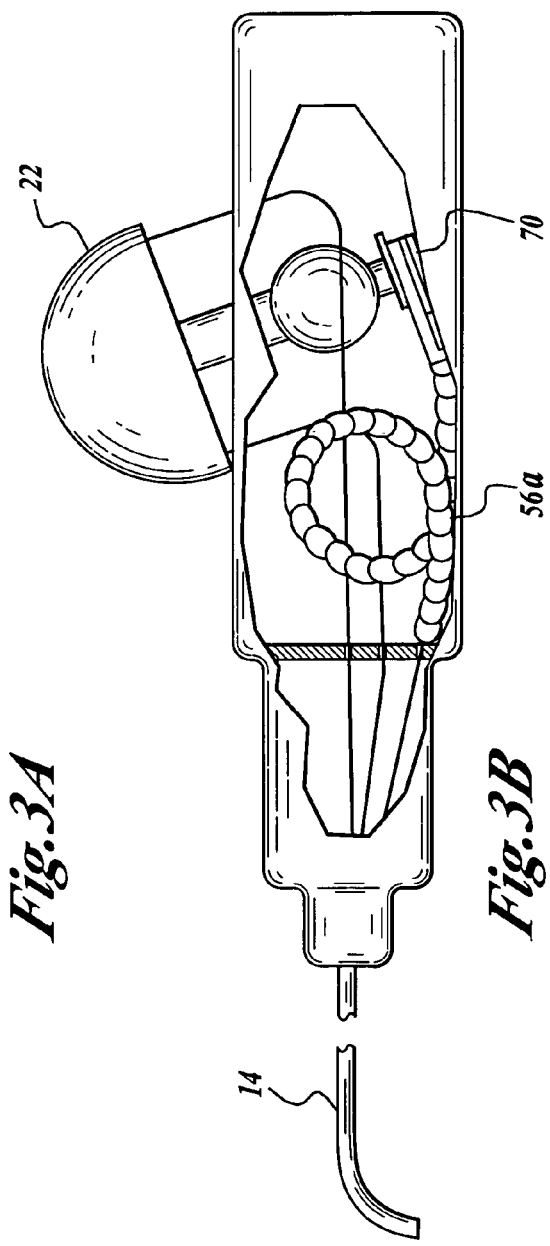

FIGS. 3A and 3B illustrate how movement of the distal tip of the medical device 14 in the left/right direction is decoupled from movement of the medical device in the up/down direction. In the embodiment shown, the control cables 56, 58 controlling the left/right movement of the medical device 14 pass through the stop plate 70. Positioned over the control cables are the outer sheaths 56a, 58a of the bowden cables (see FIG. 2). The distal ends of the outer sheaths 56a, 58a are fixed with respect to the distal end of the medical device 14. The proximal ends of the outer sheaths 56a, 58a are joined to the stop plate 70 and move with the cable guide plate 52, as it is moved back and forth within the body 12. For example, control cable 56 has an outer sheath 56a having one end secured to the stop plate 70 and another end abutting the internal wall of the body 12, as shown in FIG. 3A. The outer sheath 56a is looped to have enough slack such that as the actuator 20 is tilted or moved, the slack in the outer sheath 56a is adjusted. As will be appreciated by those skilled in the art, the amount of bend imparted by the control cables 56, 58 to the distal tip of a medical device 14 depends upon the position of the ends of the control cables 56, 58 with respect to a proximal end of the outer sheaths 56a, 58a of the bowden cables. Because the outer sheaths include a loop or slack that allows them to move as the actuator 20 is moved, this distance does not change. Therefore, a user can adjust the up/down direction of the medical device 14 by tilting the actuator 20 forwards and backwards, as indicated in FIG. 3A and FIG. 3B, while not changing the orientation of the distal tip medical device in the left/right direction. In some cases, it may be desirable to limit the movement of the looped bowden cables to prevent them from becoming pinched. Therefore, the body 12 of the controller may include a slot or other restraint to limit the movement of the outer sheaths of the control cables to a single plane.

Although the presently disclosed embodiment of the invention operates the left/right direction by rotating the cap 50 around the axis of the shaft 54, it will be appreciated that the control cables could be arranged such that rotation of the cap causes the tip to move in the up/down direction and movement of the actuator 20 back and forth causes movement in the left/right direction. Alternatively, the actuator 20 could include nested, rotatable knobs to control both the up/down and left/right directions in a manner similar to that found in conventional endoscopes. If desired, the position of the medical device in the left/right direction can be fixed with brakes, mechanical stops, or a sufficient friction force on the cap 50 so that once the desired left/right position of the medical device is determined, the position of the medical device can remain fixed if the user releases the actuator. Alternatively, a braking force can be applied to the medical device control cables in order to fix the position of the medical device. Similarly, the position of the medical device in the up/down direction can be fixed by inhibiting movement of the actuator in the forward and reverse directions, or by applying a braking force to the control cables.

Figure 4:
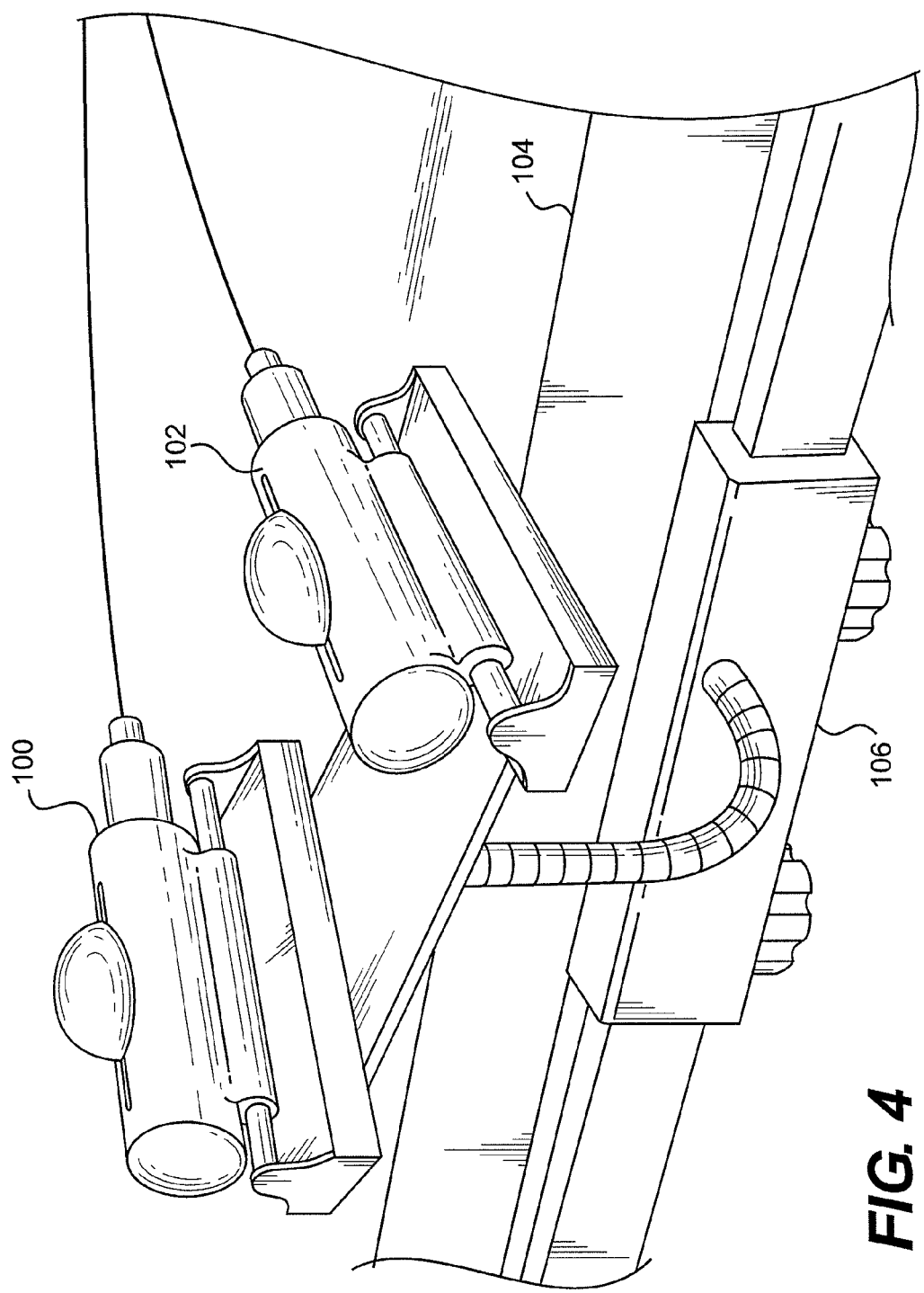
FIG. 4 illustrates how two control systems can be used by a physician.

FIG. 4 illustrates how a pair of controls 100, 102 can be secured at a fixed position with respect to a patient such as on a patient table 104 in order to allow a physician to control the orientation of a pair of medical devices. The medical devices preferably include one or more integrated instruments such as biopsy forceps, cauterizers, snares, scalpels, scissors, graspers, needle holders, staplers, fiber optic or solid state imagers etc. contained therein. Alternatively, the medical devices may be catheters that include one or more lumens 15 through which instruments can be routed. A moveable gooseneck 106 allows the position of the controls 100, 102 to be changed. Although the rails of the controls 100, 102 are shown connected to the gooseneck 106 with a pair of bases, it will be appreciated that the rails may be connected directly to a gooseneck or table 104, if desired. In yet another embodiment, one or more of the controls 100, 102 may be secured to the patient such as by strapping the controls to the patient's leg, torso, head etc. In other embodiments, the controls may be secured to the operator's body.

Figure 5:
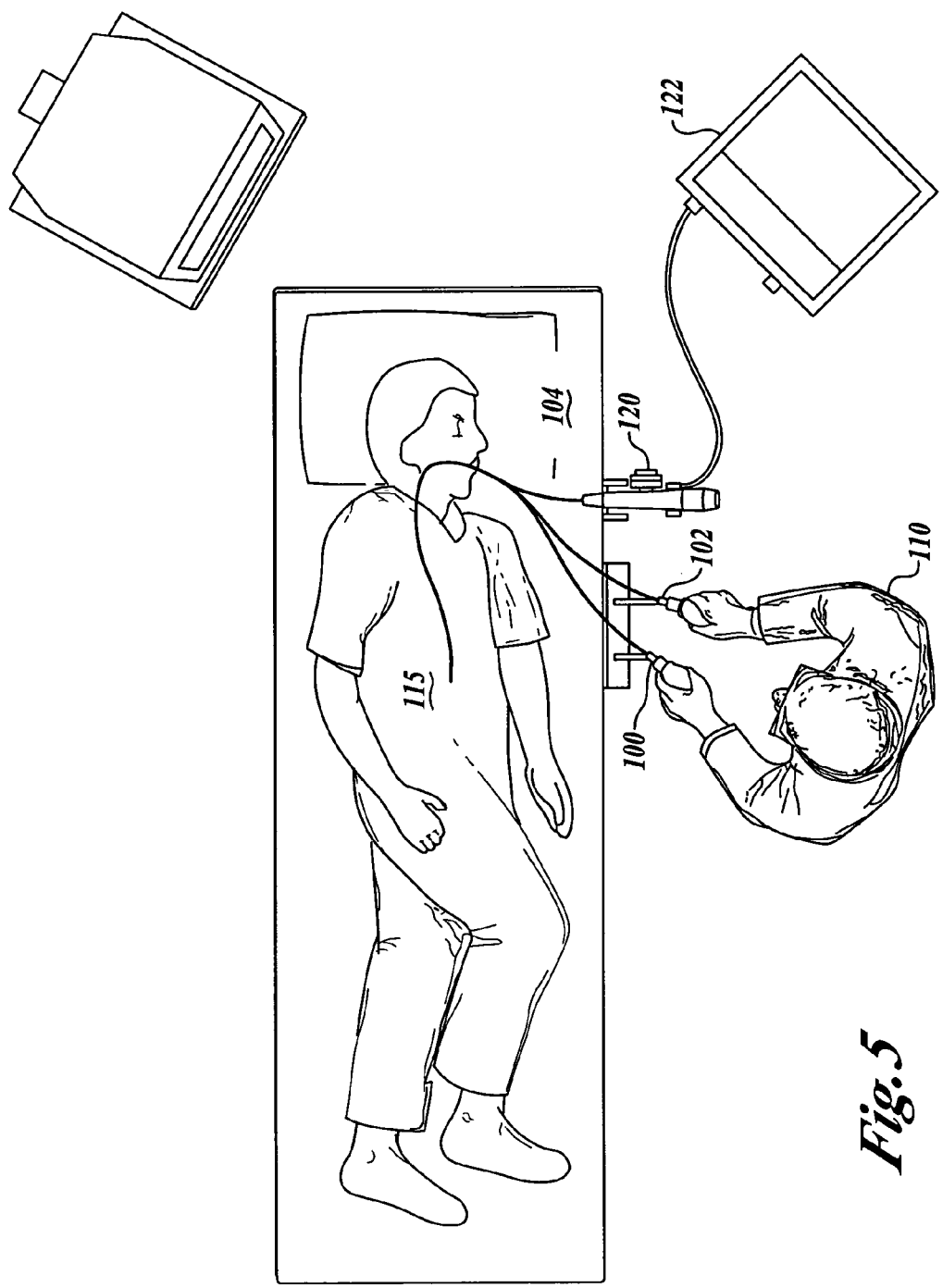
FIG. 5 illustrates how a physician operates a control system with each hand.

FIG. 5 illustrates how a physician 110 can use two hands to manipulate the pair of controls 100, 102 in order to perform a procedure within a patient 115. In practice, the medical devices controlled by the controls 100, 102 are often used in conjunction with a visualization device such as an endoscope 120 that produces images on a monitor 122 so that the physician can view the procedure. The present invention allows a physician to use two hands to control two medical devices in order to perform examinations or surgical procedures in the GI tract, colon, lungs, or through another orifice of the patient. Alternatively, the medical devices can be inserted through an incision such as with a trocar to access other areas of the body.

While the preferred embodiment of the invention has been illustrated and described, it will be appreciated that various changes can be made therein without departing from the scope of the invention. For example, additional actuator(s) could be included in the controls to tension/release control cables that terminate at other locations along the length of the medical device. For example, control cables may be secured to a location more proximal than the distal tip in order to provide bending at a more proximal portion of the device. These control cables can be tensioned with a second actuator on the control body. Alternatively, a single actuator can be used to tension more than one set of control cables. The actuator can selectively engage mechanisms to tension different control cables. Brakes or other devices can be used to fix the position of one set of control cables while the control cables from another set are adjusted. With a set of distal control cables and a set of proximal control cables, a tool in the medical device can have up to seven degrees of freedom (up/down, left/right at the distal end, up/down, left/right proximally, forward/backward, rotation about its axis and movement of the tool).

In some embodiments, movement of a medical device in the up/down, left/right direction may be controlled with actuators such as servo motors, hydraulic, pneumatic actuators disposed in a housing that is movable along and rotatable over a fixed rail in order to adjust the distal/proximal movement of a medical device as well as rotation of a device.

In addition, the controls may also include buttons, triggers or other actuators that activate particular tools such as forceps, snares, electrocauterizers, graspers, scissors, staplers etc. The actuators may be manually controlled or power assisted using pneumatics, hydraulics, motors, magnets etc. Therefore, the scope of the invention is to be determined from the following claims and equivalents thereto.

The embodiments of the invention in which an exclusive property or privilege is claimed are defined as follows:

1. A control for selectively orienting a medical device of the type having control cables operably associated with a distal tip of the medical device, comprising:
   a single actuator configured for independent longitudinal and rotational movement to direct movement of the distal tip of the medical device;
   a body coupled to the single actuator and configured to permit longitudinal and rotational movement of the single actuator;
   a first plate coupled to the single actuator that selectively tensions a first control cable when the single actuator is moved longitudinally; and
   a second plate coupled to the single actuator that selectively tensions a second control cable and does not tension the first control cable when the single actuator is moved rotationally, wherein movement of the first control cable is independent of movement of the second control cable.

2. The control of claim 1, wherein at least one of the control cables includes a bowden cable having an outer sheath.

3. The control of claim 1, further comprising:
   a rail mounted to a fixed surface with respect to a patient along which the body can be moved parallel to a longitudinal axis of the rail.

4. The control of claim 3, further comprising a clamp configured to permit rotation of the body about the longitudinal axis of the rail.

5. The control of claim 1, further comprising:
   an additional actuator configured to control the movement of another set of control cables operably associated with a distal tip of an additional medical device.

6. The control of claim 2, further comprising a stop plate configured to restrain the movement of the bowden cable.

7. The control of claim 1, wherein the medical device includes an instrument for performing an examination or procedure on a patient.

8. The control of claim 1, wherein the medical device is a catheter having one or more lumens through which an instrument can be passed.

9. A method of performing a minimally invasive procedure on a patient with one or more medical devices by:
   delivering a medical device to an internal location within the patient; and
   selectively controlling the medical device with a control that comprises:
      a single actuator configured for independent longitudinal and rotational movement to direct movement of the distal tip of the medical device;
      a body coupled to the single actuator and configured to permit longitudinal and rotational movement of the single actuator;
      a first plate coupled to the single actuator that selectively tensions a first control cable when the single actuator is moved longitudinally; and
      a second plate coupled to the single actuator that selectively tensions a second control cable and does not tension the first control cable when the single actuator is moved rotationally, wherein the movement of the first control cable is independent of movement of the second control cable.

10. The control of claim 1, wherein the body is further configured to move in at least one direction to direct movement of the distal tip of the medical device.

11. The control of claim 10, wherein the body is configured for at least one of a rotational movement and a longitudinal movement.

12. The control of claim 1, wherein the body further includes a slot configured to permit movement of the single actuator in at least two directions.

13. The control of claim 3, wherein the body includes a clamp configured to permit longitudinal movement of the body along the rail.

14. The control of claim 1, wherein the body is pivotably coupled to the single actuator by a ball joint.

* * * * *

UNITED STATES PATENT AND TRADEMARK OFFICE
CERTIFICATE OF CORRECTION

PATENT NO. : 7,618,413 B2  Page 1 of 1
APPLICATION NO. : 11/165593
DATED : November 17, 2009
INVENTOR(S) : Weitzner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 834 days.

Signed and Sealed this

Twenty-sixth Day of October, 2010

David J. Kappos
*Director of the United States Patent and Trademark Office*